(12) United States Patent
Cho et al.

(10) Patent No.: US 6,953,455 B2
(45) Date of Patent: Oct. 11, 2005

(54) MEDICINE DELIVERY SYSTEM

(75) Inventors: Steven T. Cho, Castroville, CA (US);
Keith Cromack, Gurnee, IL (US);
James Jara-Almonte, Kenosha, WI (US); Don J VerLee, Libertyville, IL (US)

(73) Assignee: Hospira, Inc., Lake Forest, IL (US)

( * ) Notice: Subject to any disclaimer, the term of this patent is extended or adjusted under 35 U.S.C. 154(b) by 246 days.

(21) Appl. No.: 10/207,934

(22) Filed: Jul. 30, 2002

(65) Prior Publication Data

US 2004/0024382 A1 Feb. 5, 2004

(51) Int. Cl.$^7$ .............................................. A61K 9/22
(52) U.S. Cl. ................................. 604/890.1; 604/93.01
(58) Field of Search .................... 604/890.1–892.1, 604/65, 66, 88, 82, 244, 246, 288.01, 304–307, 288.04, 93.01; 137/68.11, 68.13; 222/541.1; 219/209; 216/2, 39, 56

(56) References Cited

U.S. PATENT DOCUMENTS

| | | | |
|---|---|---|---|
| 4,198,135 A | | 4/1980 | Erlichman |
| 5,059,175 A | | 10/1991 | Hanover et al. |
| 5,167,625 A | | 12/1992 | Jacobsen et al. |
| 5,366,454 A | * | 11/1994 | Currie et al. ............ 604/890.1 |
| 5,368,704 A | | 11/1994 | Madou et al. |
| 5,443,508 A | | 8/1995 | Giampapa |
| 5,797,898 A | | 8/1998 | Santini, Jr. et al. |
| 6,114,658 A | | 9/2000 | Roth et al. |
| 6,123,861 A | * | 9/2000 | Santini, Jr. et al. .............. 216/2 |
| 6,247,485 B1 | | 6/2001 | Rossi et al. |
| 6,491,666 B1 | * | 12/2002 | Santini, Jr. et al. .......... 604/191 |
| 6,527,762 B1 | * | 3/2003 | Santini, Jr. et al. ...... 604/890.1 |
| 6,551,838 B2 | * | 4/2003 | Santini, Jr. et al. .......... 436/174 |
| 6,656,162 B2 | * | 12/2003 | Santini et al. .............. 604/191 |
| 6,708,050 B2 | * | 3/2004 | Carim ......................... 600/372 |
| 6,730,072 B2 | * | 5/2004 | Shawgo et al. .......... 604/890.1 |
| 6,808,522 B2 | * | 10/2004 | Richards et al. ......... 604/890.1 |
| 2002/0072784 A1 | * | 6/2002 | Sheppard et al. ............ 607/60 |
| 2002/0107470 A1 | * | 8/2002 | Richards et al. ............ 604/20 |
| 2002/0119176 A1 | * | 8/2002 | Greenberg et al. .......... 424/422 |
| 2002/0183721 A1 | * | 12/2002 | Santini et al. ........... 604/890.1 |
| 2002/0187260 A1 | * | 12/2002 | Sheppard et al. ........ 427/248.1 |
| 2003/0010808 A1 | * | 1/2003 | Uhland et al. ........... 228/110.1 |
| 2003/0036746 A1 | * | 2/2003 | Penner et al. ............ 604/891.1 |
| 2003/0077440 A1 | * | 4/2003 | Razavi ....................... 428/343 |
| 2003/0158584 A1 | * | 8/2003 | Cates et al. .................... 607/2 |
| 2003/0233862 A1 | * | 12/2003 | Wise et al. ................ 73/23.39 |
| 2004/0043042 A1 | * | 3/2004 | Johnson et al. ............. 424/400 |

FOREIGN PATENT DOCUMENTS

| | | |
|---|---|---|
| WO | 01/35928 | 5/2001 |
| WO | 02/099457 | 12/2002 |

* cited by examiner

*Primary Examiner*—Nicholas D. Lucchesi
*Assistant Examiner*—Cris L. Rodriguez
(74) *Attorney, Agent, or Firm*—Michael R. Crabb

(57) ABSTRACT

A medicine delivery system (10) implantable into a human or animal body includes a medicine delivery unit (14) and a control unit (12). A membrane (26) seals the delivery opening (22) of a medicine compartment (18) and is pre-stressed by an amount less than the predetermined elastic deformation and rupture point limits of the membrane (26). A release element (28) associated with compartment (18) causes the membrane (26) to be stressed beyond the deformation and rupture point limits in response to a control signal (78). Release element (28) ruptures the membrane (26) along a predetermined rupture pattern to permit a first membrane portion (35), forming a hinged lid, to separate from a second membrane portion (37) along the predetermined rupture pattern while remaining attached to the second membrane portion at a hinge (39).

16 Claims, 6 Drawing Sheets

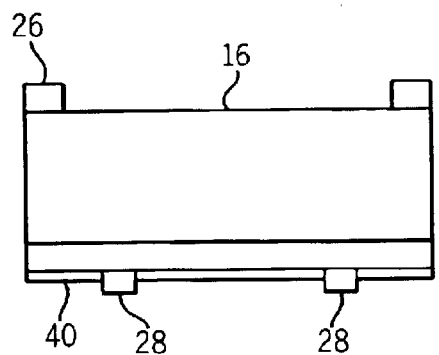
FIG. 7F
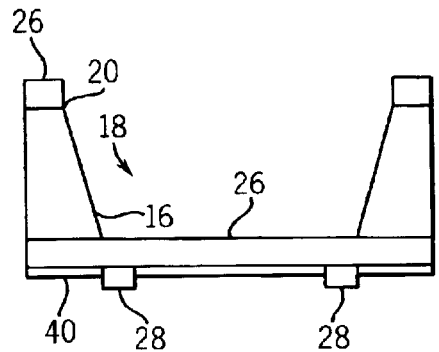
FIG. 7G
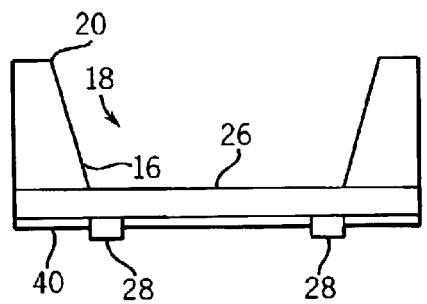
FIG. 7H
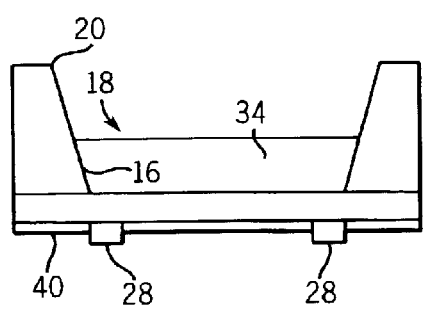
FIG. 7I
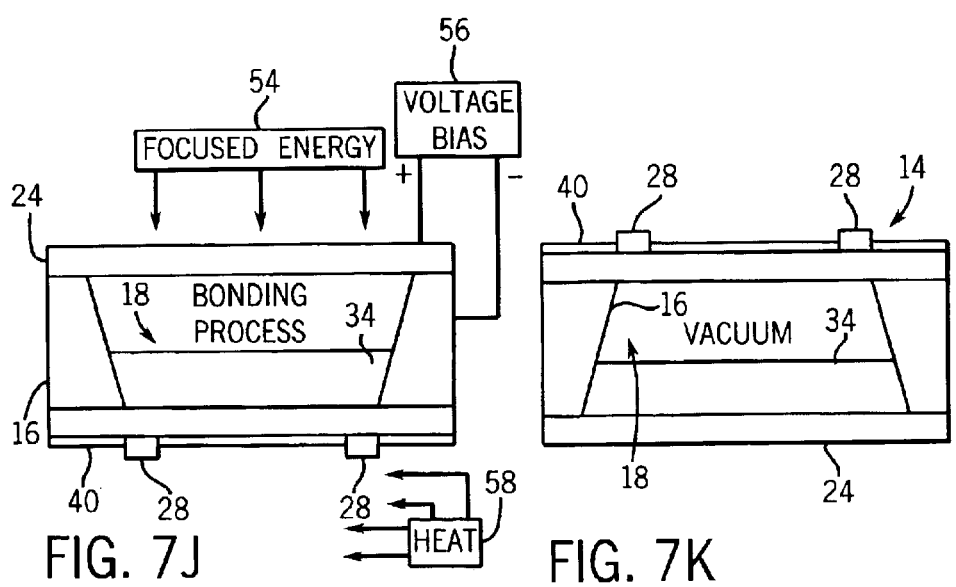
FIG. 7J
FIG. 7K

MEDICINE DELIVERY SYSTEM

FIELD OF THE INVENTION

The present invention generally relates to medicine delivery systems suitable for fabrication using micro-electro-mechanical system (MEMS) technology. More particularly, the present invention relates to a medicine delivery system, adapted to be implanted into a human or an animal, for controlling the delivery of a medicine to the human or the animal at specific times and rates by rupturing a membrane, without permitting the ruptured membrane to separate from the medicine delivery system and be released in the animal or human.

BACKGROUND OF THE INVENTION

Medicine delivery is an important aspect of medical treatment. The efficacy of many medicines is directly related to the way in which they are administered. Some therapies require that the medicine be repeatedly administered to the patient over a long period of time. This makes the selection of a proper medicine delivery method problematic. Patients often forget, are unwilling, or are unable to take their medication. Medicine delivery also becomes problematic when the medicines are too potent for systemic delivery. Therefore, attempts have been made to design and fabricate a delivery device that is capable of the controlled, periodic or continuous release of a wide variety of molecules including, but not limited to, drugs and other therapeutics.

Micro-electro-mechanical system (MEMS) technology integrates electrical components and mechanical components on a common silicon substrate using microfabrication technology. Integrated circuit (IC) fabrication processes, such as photolithography processes and other microelectronic processes, form the electrical components. The IC fabrication processes typically use materials such as silicon, glass, and polymners. Micromachining processes, compatible with the IC processes, selectively etch away areas of the IC or add new structural layers to the IC to form the mechanical components. The integration of silicon-based microelectronics with micromachining technology permits complete electromechanical systems to be fabricated on a single chip. Such single chip systems integrate the computational ability of microelectronics with the mechanical sensing and control capabilities of micromachining to provide smart devices small enough to be implanted inside of a human or animal.

Examples of implantable medicine delivery systems suitable for fabrication using micro-electro-mechanical system (MEMS) technology are described in U.S. Pat. No. 5,366,454 (Currie, et al.), and U.S. Pat. No. 6,123,861 (Santini, Jr., et al.). These patents are described as improvements over non-MEMS type of electromechanical devices that are larger and less reliable and controlled release polymeric devices, designed to provide medicine release over a period of time via diffusion of the medicine through the polymer and/or degradation of the polymer over the desired time period following administration to the patient.

U.S. Pat. No. 5,366,454 (Currie, et al.) discloses a medication dispensing device for implantation into an animal or human body, and including a substrate having a plurality of compartments, a closure member, a rupturable membrane and a membrane rupturing system. Each compartment has a charging opening for charging the compartment with a dose of medicine and a delivery opening permitting delivery of the medicine. The closure member, made of silicon, is anodically bonded to the substrate, also made of silicon, for sealing the charging openings of the compartments. The membrane, made of silicon, may be integrally formed with the substrate or anodically bonded to the substrate, also made of silicon, for sealing the delivery openings of the compartments. The membrane has a predetermined elastic deformation limit and a predetermined rupture point. A "V-shaped" groove is formed in the membrane to define a line of weakness to assist the rupture of the membrane. The membrane rupturing system associated with each compartment ruptures the membrane thereof in response to an electrical signal. The membrane rupturing system includes a stress-inducing member maintaining the membrane stressed to substantially the elastic deformation limit thereof, and a piezoelectric transducer responsive to the electrical signal for applying to the membrane additional stress sufficient to exceed the rupture point of the membrane, thereby causing the membrane to rupture. Upon rupture of the membrane, body fluids are permitted to enter into the compartment for mixing with the medicine contained therein so that the medicine is released in admixture with the body fluids through the delivery opening into the animal or human body. The device further includes a control circuit connected to a power source for supplying the electrical signal to a respective piezoelectric transducer of each membrane rupturing system to activate the respective piezoelectric transducer. A biologically compatible polymeric film covers the membrane to bind any broken membrane fragments to the device and to prevent the fragments from being released into the human or animal.

U.S. Pat. No. 6,123,861 (Santini, Jr., et al.) discloses a microchip drug delivery device for controlling the rate and time of delivery of molecules, such as medicines, in either a periodic or continuous manner. This device typically includes hundreds to thousands of reservoirs, or wells, formed in a silicon substrate containing the molecules and a release element that controls the rate of release of the molecules. The reservoirs can contain multiple medicines or other molecules in variable dosages. The filled reservoirs can be capped with materials that passively disintegrate, materials that allow the molecules to diffuse passively out of the reservoir over time, or materials that disintegrate upon application of an electric potential. Release from an active device can be controlled by a preprogrammed microprocessor, remote control, or by biosensors.

Several methods are used to bond silicon wafers together or to other substrates, such as glass substrates, to form larger or more complex micromachined systems, such as medicine delivery systems, including: adhesion bonding, anodic bonding, eutectic bonding, glass-frit bonding, fusion bonding, low temperature fusion bonding, and microwave bonding. Among these various bonding methods engineering tradeoffs exist for the applied temperature, applied voltage, applied pressure, applied energy, bonding time, bond strength, material cost, etc.

Adhesion bonding uses an adhesive to bond the substrates together. This is typically done by spin coating a thin film of adhesive on one or both substrates before they are brought into contact. The substrates are typically baked at a prescribed temperature to cure the adhesive.

Anodic bonding, otherwise known as electrostatic bonding, typically hermetically and permanently joins glass to silicon substrates without using adhesives. The glass substrate contains typically has a high percentage of alkali metals, such as sodium oxide. The silicon and glass substrates are brought into contact with each other. The silicon and glass substrates are heated to a temperature (typically in the range 300–500° C. depending on the glass type) above the softening point of the glass substrate that results in the sodium oxide splitting up into sodium and oxygen ions. A high DC voltage (e.g., up to 1 kV) is applied across the substrates creating an electrical field that penetrates the substrates. The electric field causes the sodium ions to migrate from the interface between the substrates towards the cathode where they are neutralized providing a depletion layer with high electric field strength. The resulting electrostatic attraction at the depletion layer brings the silicon and glass into intimate contact. The electric field also causes the oxygen ions to flow from the glass substrate to the silicon substrate resulting in an anodic reaction at the interface with the silicon ions in the silicon substrate to form irreversible silicon-oxygen-silicon bonds. The result is that the glass substrate is bonded to the silicon substrate with a permanent chemical bond. The disadvantages of anodic bonding include the relatively high temperature required, temperature non-uniformity during vacuum sealing, and relatively long bond times (e.g., 10 minutes).

Eutectic bonding and glass-frit bonding use a film of metal and glass ceramic adhesive, respectively, to hermetically seal the substrates together under high temperature.

Fusion bonding uses two silicon substrates having hydrophobic or hydrophilic, mirror-polished, flat and clean surfaces. The two surfaces of the substrates contact each other under high pressure creating atomic attraction forces that bond the two substrates together. The atomic attraction forces are strong enough to allow the bonded substrates to be moved to a furnace. The bonded substrates are annealed at high temperature (e.g., 900° C.–1100° C.) in the furnace to form a solid hermetic seal between the two substrates.

Low temperature fusion bonding advances the glass-frit bonding process. In contrast to the glass-frit bonding process, low temperature fusion bonding does not use a glass ceramic adhesive to bond the substrates together. The low temperature fusion bonding process uses low heat to soften the substrates, and pressure to squeeze and hold the substrates together until they bond over a prescribed period of time.

Microwave bonding uses electromagnetic energy to bond two metallized dielectric or silicon substrates to each other. The electromagnetic energy in the form of a pulse heats the metallic interface between the two substrates to melt the interface together while permitting the substrates to remain cool.

It would be desirable to have a medicine delivery system, adapted to be implanted in a human or animal, that actively releases a drug or other molecule into the animal or human by rupturing a membrane, without permitting the ruptured membrane to separate from the medicine delivery system and to be released in the animal or human. Such a system would not permit disintegrated membrane material to separate from the drug delivery device to be released in the animal or human, as disclosed in U.S. Pat. No. 6,123,861 (Santini, Jr., et al.). Further, such a system would not require the biologically compatible polymeric film shown as necessary by U.S. Pat. No. 5,366,454 (Currie, et al.) to bind any broken membrane fragments to the device and to prevent the fragments from being released into the human or animal.

It would also be desirable to have a bonding process to hermetically seal two substrates together at a temperature lower than the 300–500° C. range used for anodic bonding. Such a bonding process would not damage thermally degraded materials, such as the medicine in the medication dispensing device as disclosed in U.S. Pat. No. 5,366,454 (Currie, et al.). Such a bonding process would also be fast to provide high manufacturing throughput. Further, such a process would also apply a relatively low pressure to the substrates.

SUMMARY OF THE INVENTION

According to one aspect of the present invention, a medicine delivery system delivers drugs and other molecules reliably for weeks or years at a time.

According to another aspect of the present invention, the medicine deivery system permits delivery of medicines in either a periodic or continuous manner.

According to another aspect of the present invention, the medicine delivery system holds many different medicines of varying dosages.

According to another aspect of the present invention, the medicine delivery system is small enough to be implanted, injected or swallowed, if desired.

According to another aspect of the present invention, the medicine delivery system delivers the medicine by rupturing a membrane, without permitting the ruptured membrane to separate from the medicine delivery system.

According to another aspect of the present invention, the medicine delivery system includes a control unit and a medicine delivery unit. The medicine delivery unit includes a plurality of compartments, a membrane and a plurality of release elements. The control unit is adapted to generate a control signal. Each compartment is adapted to contain a predetermined amount of a medicine and has a delivery opening permitting delivery of the medicine. The membrane is adapted to seal the delivery opening of each compartment. Each release element is associated with a corresponding compartment. The release element is adapted to rupture the membrane along a predetermined rupture pattern responsive to the control signal. A first membrane portion partially separates from a second membrane portion along the predetermined rupture pattern, while remaining attached to the second membrane portion at a connection area. The rupture of the membrane permits body fluids of the human or animal to mix with the medicine so that the medicine is released in admixture with the body fluids through the delivery opening into the human or animal body.

These and other aspects of the present invention are further described with reference to the following detailed description and the accompanying figures, wherein the same reference numbers are assigned to the same features or elements illustrated in different figures. Note that the figures may not be drawn to scale. Further, there may be other embodiments of the present invention explicitly or implicitly described in the specification that are not specifically illustrated in the figures and vice versa.

BRIEF DESCRIPTION OF THE DRAWINGS

FIGS. 7A–7K illustrate, in a sequence of steps, a MEMS fabrication process for making the medicine delivery unit, as shown in FIGS. 1–6, in accordance with the preferred embodiment of the present invention. Cross-hatching has been omitted for the sake of clarity.

DETAILED DESCRIPTION OF THE PREFERRED EMBODIMENTS

Figure 1:
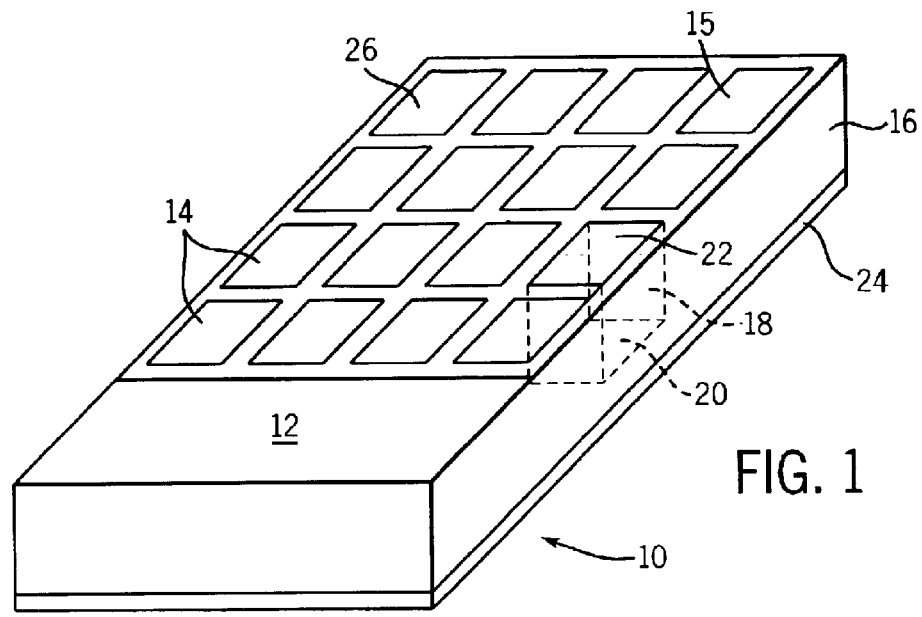
FIG. 1 illustrates a perspective view of a medicine delivery system, including a control unit and a plurality of medicine delivery units, in accordance with a preferred embodiment of the present invention.

FIG. 1 illustrates a perspective view of a medicine delivery system 10, including a control unit 12 and a plurality of spaced-apart medicine delivery units 14, in accordance with a preferred embodiment of the present invention. The medicine delivery system 10 is fabricated using the MEMS technology, as described above, using methods commonly applied to the manufacture of integrated circuits such as ultraviolet (UV) photolithography, reactive ion etching, and electron beam evaporation, as are well known in the art. The MEMS technology fabrication procedure permits the manufacture of medicine delivery systems 10 with primary dimensions (length of a side if square or rectangular, or diameter if circular) ranging from less than a millimeter to several centimeters. The thickness of a typical medicine delivery system 10 is 300 micrometers, but can vary from approximately 10 micrometers to several millimeters, depending on the system's application. Changing the system thickness affects the maximum number of medicine delivery units 14 that may be incorporated into the system and the volume of each medicine delivery unit 14. "In body" applications of the device would typically require systems having a primary dimension of 2 cm or smaller. Systems for in body applications are small enough to be swallowed or implanted using minimally invasive procedures. Smaller in body systems (on the order of a millimeter) can be implanted using a catheter or other injection means.

Preferably, the medicine delivery system 10 has a small wafer-like substrate 16 providing the plurality of spaced-apart medicine delivery units 14. The substrate 16 serves as a support for the medicine delivery device 10. The substrate 16 may be any material that is suitable for etching or machining, for providing a support, and is impermeable to medicines and to surrounding body fluids, such as, water, blood, electrolytes or other solutions. Examples of materials, suitable for the substrate 16, include, without limitation, ceramics, semiconductors, glass, and degradable and non-degradable polymers.

Biocompatibility of the substrate material is preferred, but not required. For in body applications, non-biocompatible materials may be encapsulated in a biocompatible material, such as poly(ethylene glycol) or polytetrafluoroethylene-like materials, before use. Silicon is an example of a material that forms a strong, non-degradable, easily etched substrate that is impermeable to the enclosed medicines and the surrounding body fluids. Poly(anhydride-co-imide) is an example of a material that forms a strong substrate that degrades or dissolves over a period of time into biocompatible components. This material is preferred for in body applications where the system is implanted and physical removal of the device at a later time is not feasible or recommended.

Each medicine delivery unit 14 has a compartment 18, adapted to contain or enclose a medicine 34 (shown in FIGS. 4–7), which is defined by a cavity, a recess, or a reservoir formed in the substrate 16 by etching, machining, or other known process. The compartments 18 are each provided with a charging opening 20 permitting receipt of medicine 34 in the compartment 18, and with a delivery opening 22 permitting delivery of the medicine contained therein. A cap 24 seals the charging openings 20, preferably using a bonding method described in FIG. 8, or a waterproof epoxy or other appropriate material impervious to the surrounding fluids. A membrane 26 seals the delivery openings 22.

Figure 4:
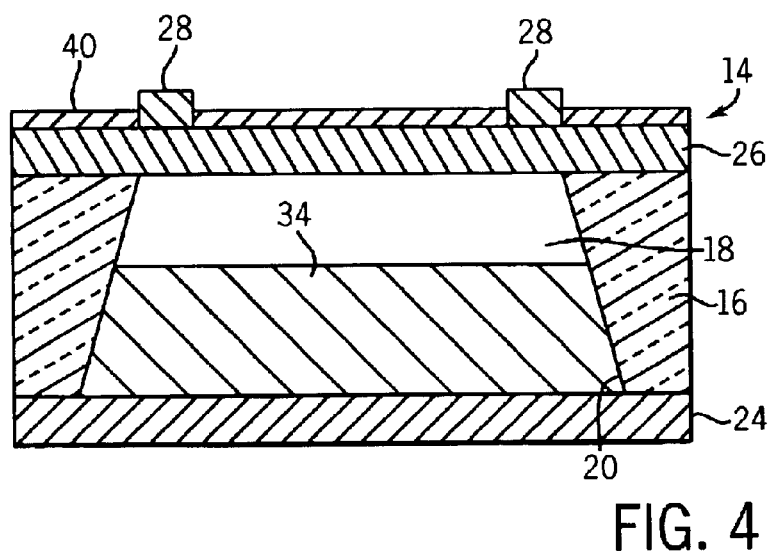
FIG. 4 illustrates a magnified lateral cross-sectional view of the medicine delivery unit taken along line 4—4 in FIG. 3.

As best seen in FIG. 4, the medicine 34 is inserted into the charging opening 20 of the compartment 18 by any method including, without limitation, injection, inkjet printing, spin coating, capillary action, pulling or pushing the medicine using a vacuum or other pressure mechanism, melting the material into the compartment 18, centrifugation and related processes, packing solids into the compartment 18, or any combination of these or other similar filling techniques.

The medicine 34 may be a solid, liquid or gel in the compartments 18. Preferably, the medicine 34 is formed as a solid because the solid medicine has a high concentration per unit volume, such as for example in the pico-gram range. The medicine 34 may be any natural, synthetic, or semi-synthetic compound or mixture thereof that can be delivered. In one embodiment, the medicine delivery system 10 is used to deliver medicines systemically to a patient in need thereof. In another embodiment, the construction and placement of the medicine delivery system 10 in a patient enables the localized release of medicines 34 that may be too potent for systemic delivery. As used herein, medicines are compounds or salts, prodrugs, solvates, salts and/or solvates of prodrugs thereof, including, without limitation, proteins, nucleic acids, polysaccharides and synthetic organic molecules, having a bioactive effect, for example, anesthetics, vaccines, chemotherapeutic agents, hormones, metabolites, sugars, immunomodulators, antioxidants, ion channel regulators, and antibiotics. The medicines 34 can be in the form of a single medicine or medicine mixtures and can include pharmaceutically acceptable carriers. In another embodiment, molecules are released in body in any system where the controlled release of a small (milligram to nanogram) amount of one or more molecules is required, for example, in the fields of analytic chemistry or medical diagnostics. Molecules can be effective as pH buffering agents, diagnostic agents, and reagents in complex reactions such as the polymerase chain reaction or other nucleic acid amplification procedures.

Each compartment 18 may contain different medicines 34 depending on the medical needs of the patient or other requirements of the medicine delivery system 10. For applications in medicine delivery, for example, the medicines 34 in each of the rows can differ from each other. Further, the rate of the release of the medicine 34 may differ within each row to release a medicine at a fast rate from one compartment 18 and a slow rate from another compartment 18. Each compartment 18 may also contain different dosages of the medicines 34. The dosages may also vary within each row of medicine delivery units 14.

For in body applications, the entire medicine delivery system 10, except for the side of the medicine delivery system 10 providing the delivery openings 22 on the medicine delivery units 14, is encased in a material appropriate for the system 10. For in body applications, the medicine delivery system 10 is preferably encapsulated in a biocompatible material such as poly(ethylene glycol) or polytetrafluoroethylene.

Use of MEMS technology fabrication techniques permit the incorporation of hundreds to thousands of compartments 18 in a single medicine delivery system 10. The spacing between each compartment 18 depends on its particular application and whether or not the release of the medicine is active or passive. With an active release, the distance between the reservoirs may be slightly larger (between approximately 1 and 10 micrometer) than with a passive release due to the space occupied by a release element (not shown in FIG. 1) on or near each compartment 18. The compartments 18 may be made in nearly any shape and depth, and need not pass completely through the substrate 16. In a preferred embodiment, the compartments 18 are etched into a silicon substrate by potassium hydroxide in the shape of a square pyramid, having side walls sloped at approximately fifty-four degrees, which pass completely through the substrate (approximately 300 micrometers) to the membrane 26 on the other side of the substrate 16, as shown in FIG. 7. The pyramidal shape permits easy filling of the compartments 18 through the charging opening 20 (approximately 500 micrometers by 500 micrometers) on a patterned side of the substrate 16, release through the delivery opening 22 (approximately 50 micrometers by 50 micrometers) on the other side of the substrate 16, and provides a large cavity inside the medicine delivery unit 14 for storing the medicine.

Figure 2:
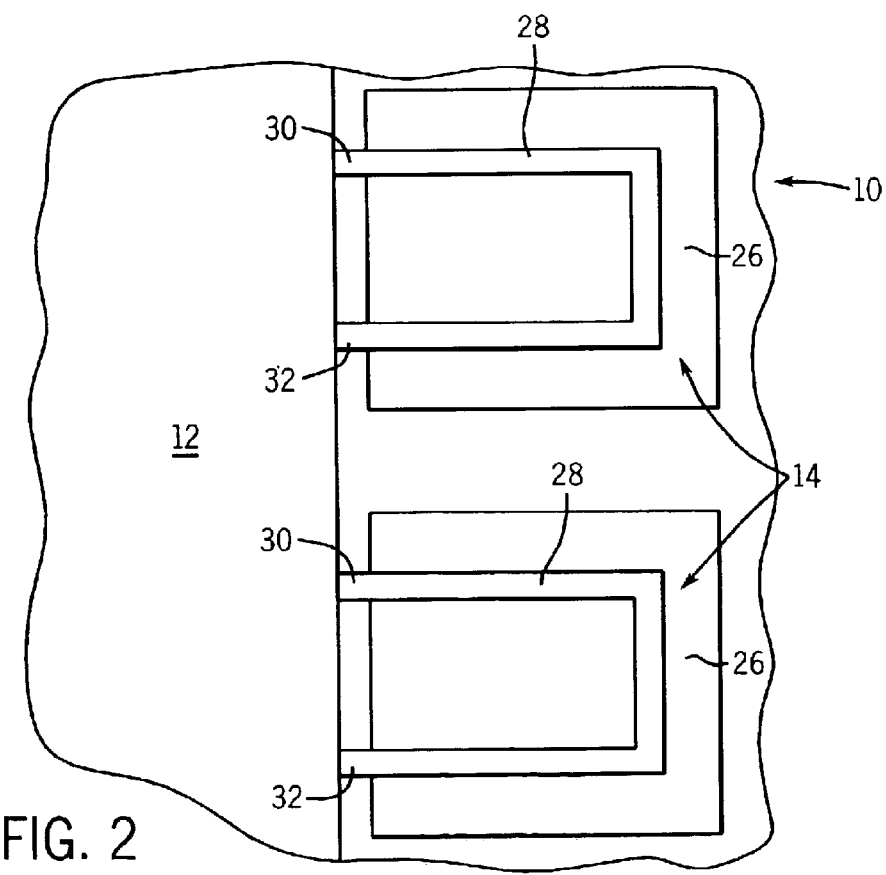
FIG. 2 illustrates a magnified partial top plan view of the medicine delivery system of FIG. 1.
Figure 3:
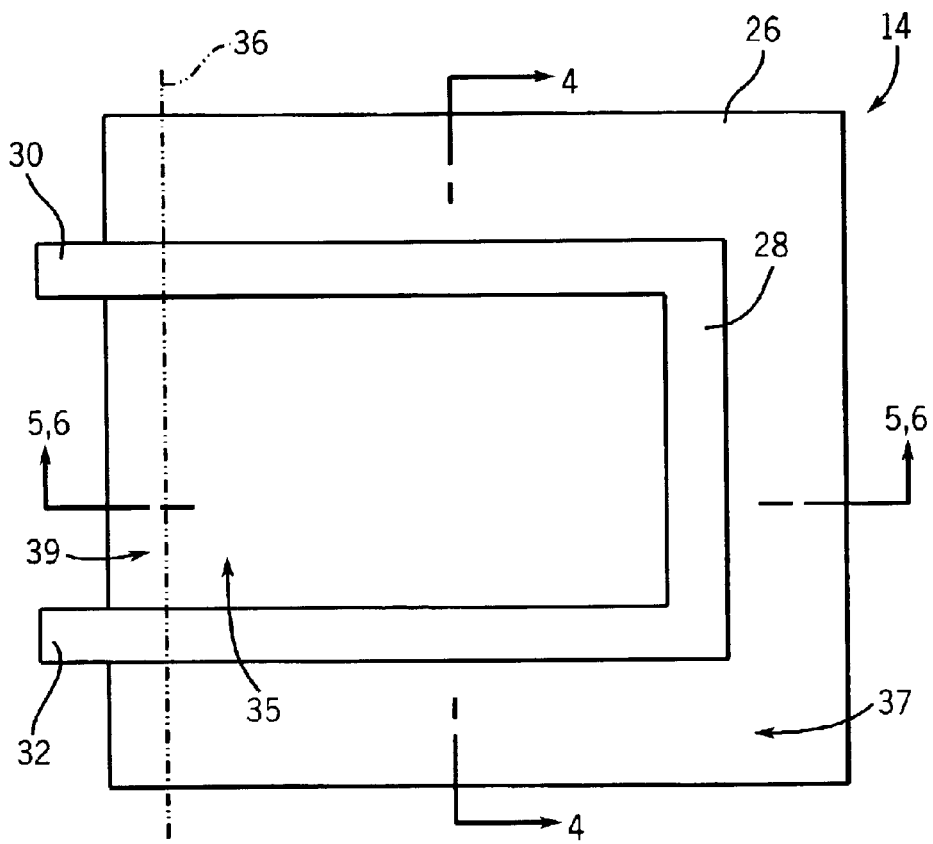
FIG. 3 illustrates a magnified top plan view of a medicine delivery unit, as shown in FIGS. 1 and 2, having a release element disposed on a membrane.
Figure 5:
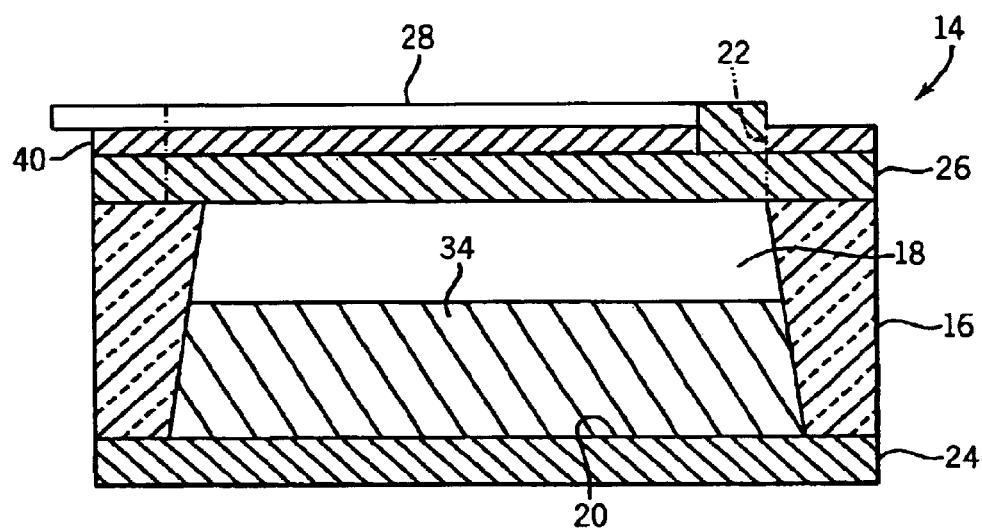
FIG. 5 illustrates a longitudinal cross-sectional view of the medicine delivery unit taken along line 5—5 in FIG. 3, before the membrane is ruptured.
Figure 6:
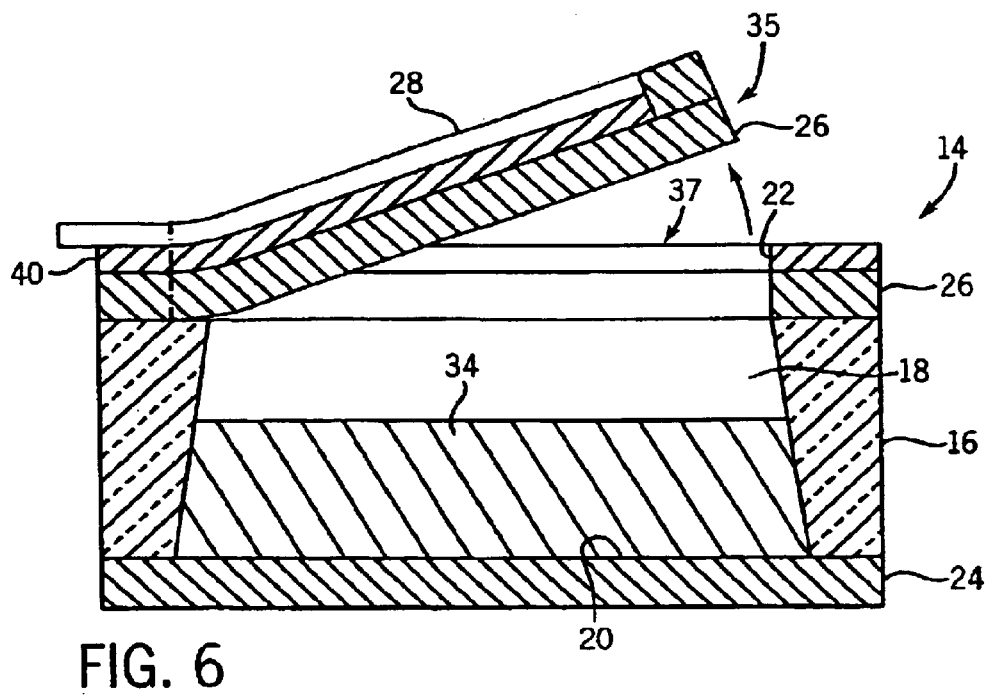
FIG. 6 is a longitudinal cross-sectional view similar to FIG. 5 but shows the medicine delivery unit after the membrane is ruptured.

Referring next to FIGS. 2–6, FIG. 2 illustrates a magnified partial top plan view of the medicine delivery system 10, of FIG. 1. FIG. 3 illustrates a magnified top plan view of a medicine delivery unit 14, as shown in FIGS. 1 and 2, having a release element 28 disposed on the membrane 26. FIG. 4 illustrates a magnified lateral cross-sectional view of the medicine delivery unit 14, as shown in FIG. 3, having the release element 28 disposed on the membrane 26. FIG. 5 illustrates a longitudinal elevation view of the medicine delivery unit 14, as shown in FIG. 3, before the membrane 26 is ruptured, in accordance with the preferred embodiment of the present invention. FIG. 6 illustrates the longitudinal elevation view of the medicine delivery unit 14, as shown in FIG. 3, after the membrane 26 is ruptured, in accordance with the preferred embodiment of the present invention.

The release element 28 is associated with each medicine delivery unit 14 for rupturing the membrane 26 in response to a control signal 78 (shown in FIG. 9) from the control unit 12. The size, shape and placement of the release element 28 may vary, depending on various engineering considerations for the particular application. The release element 28 is preferably disposed on the membrane 26, either inside and/or outside the compartment 18, using deposition techniques such as chemical vapor deposition, electron or ion beam evaporation, sputtering, spin coating, and other techniques known in the art. Various release elements may be used to rupture the membrane 26 including, without limitation, electrostatic, magnetic, piezoelectric, bimorph, shape memory alloys, temperature, chemical, and other mechanisms that cause stress or strain on the membrane 26.

When a temperature element such as a polysilicon piezoresistor is used as the release element 28 a thermal insulator, such as silicon dioxide, may be used as the membrane 26 to isolate the temperature element from the medicine 34, if desired. The substrate 16 is preferably formed of silicon and acts as a heat sink. The thermal conductivity for silicon is 1.57 W/cm-degrees C., for silicon dioxide is 0.014 W/cm-degrees C., and for polysilicon is 0.17 W/cm-degrees C. When the temperature element 28 is heated, the membrane 26 cracks due to the high thermal gradient induced stresses on the membrane 26 causing the medicine delivery unit 14 to open. A thin film of tensile silicon nitride may be applied to the membrane 26 to assist in opening the medicine delivery unit 14 when the temperature element is heated. After the membrane 26 is ruptured, the tensile silicon nitride pulls the membrane 26 back to assist in forming the delivery opening 22.

The release element 28 is electrically coupled to the control unit 12 via electrodes 30 and 32. Exemplary conductive materials for the electrodes include metals such as copper, gold, silver, and zinc and some polymers. Typical film thickness of the electrodes 30 and 32 may range from 0.05 to several microns. When an electric potential is applied to the electrodes 30 and 32, the membrane 26 ruptures along a predetermined pattern to expose the compartment 18 containing the medicine 34 to the surrounding fluids.

The predetermined rupture pattern preferably approximates the size and shape of the release element 28. Preferably, the predetermined rupture pattern has a width in the range of 2 to 20 micrometers, a length of a side of the delivery opening 22 in the range of 40 to 500 micrometers, and spacing between the predetermined rupture pattern and the edge of the delivery opening 22 in the range of 2 to 20 micrometers.

An insulating or dielectric material 40 such as silicon oxide ($SiO_2$) or silicon nitride ($SiN_2$) is deposited over the entire surface of the medicine delivery system 10 by methods such as chemical vapor deposition, electron or ion beam evaporation, sputtering, or spin coating and other techniques known in the art. Photoresist (not shown) is patterned on top of the dielectric material 40 to protect it from etching except on the release element 28 directly over each compartment 18. The dielectric material 40 can be etched by plasma, ion beam, or chemical etching techniques. The purpose of this dielectric material 40 and photoresist film is to protect the electrodes 30 and 32 from corrosion, degradation, or dissolution in all areas where electrode film removal is not necessary for release of the medicine 34.

The membrane 26 has a predetermined elastic deformation limit and a predetermined rupture point. The membrane 26 may be formed of a variety of materials including, without limitation, dielectric, polysilicon or silicon. The membrane 26 may have a line of weakness formed therein along the predetermined rupture pattern to assist with rupturing the membrane 26. Preferably, the membrane 26 is thinner at the line of weakness than at other areas of the membrane 26. Such thinning may be formed by a V-shaped indentation in the membrane 26. Preferably, the membrane 26 is integrally formed with the substrate 16. Alternatively, the membrane 26, can be formed separately from the substrate 16 and bonded thereto, such as with a membrane, formed of silicon, anodically bonded to a substrate 16, also formed of silicon.

Preferably, the membrane 26 is hermetically sealed over the delivery openings 22 to form a vacuum in the compartments 18. Various mechanisms for forming the vacuum seal include, without limitation, wide area heating mechanisms such as electrostatic bonding, and local area heating sources such as laser, microwave, and infrared energy. The local area heating mechanisms are preferred over the wide area heating mechanisms because the local area heating mechanisms operate at a lower temperature (e.g., 100–150 degrees C.) rather than at a higher temperature (e.g., 300–400 degrees C.). Using the lower temperature over the local area prevents damage to the medicine delivery unit 10 and to the medicine 34, and creates more strain on the membrane 26 due to the high temperature gradient along the membrane 26 from the local area to the center of the membrane 26. In this case, each compartment 18 is drawn under a vacuum causing the membrane 26 to be drawn inward into the compartment 18 forming a concave shape. Under the vacuum, the membrane 26 is strained to a point near to but less than the predetermined elastic deformation limit and the predetermined rupture point of the membrane 26. Since the compartment 18 is under vacuum, the membrane 26 is in a pre-stressed condition. The release element 28 causes the membrane 26 to bend past its yield point resulting the membrane 26 rupturing along the predetermined pattern. Because the membrane 26 is already in a pre-stressed state, the release element 28 does not require as much energy to rupture the membrane 26, as compared to a membrane 26 that is not in a pre-stressed state.

The membrane 26 has a first portion 35 located inside the predetermined pattern and a second portion 37 located outside the predetermined pattern. The first portion 35 of the membrane 26 is attached to the second portion 37 of the membrane 26 at a connection area 39. In the preferred embodiment of the present invention, the first portion 35 of the membrane 26 forms a lid and the connection area 39 forms a hinge 36. When the membrane 26 ruptures, the lid separates from the second portion 37 of the membrane 26, except at the hinge 36, to permit the medicine 34 to be delivered through the delivery opening 22, as shown in FIG. 6. The hinge 36 permits the lid to remain attached to the medicine delivery system 10 so that it is not released in the animal or human. The first portion 35 of the membrane 26 and the connection area 39 may have various sizes, shapes and positions, depending on various engineering considerations for a particular application.

Figure 7A:
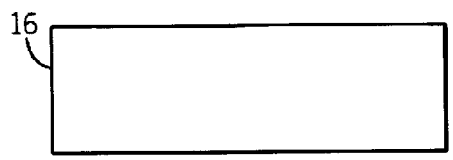
Figure 7B:
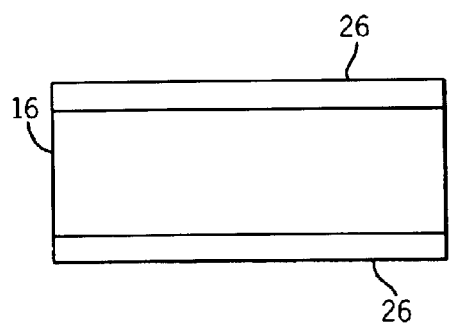
Figure 7C:
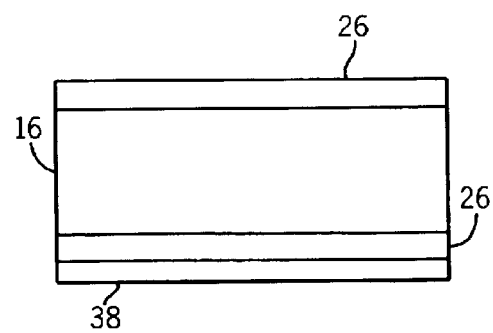
Figure 7D:
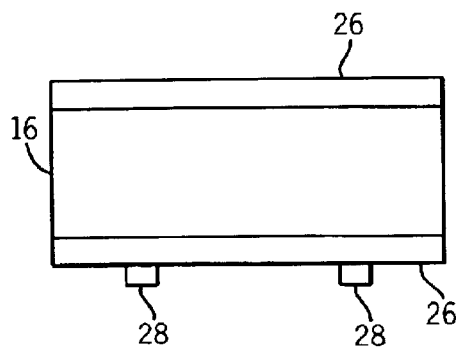
Figure 7E:
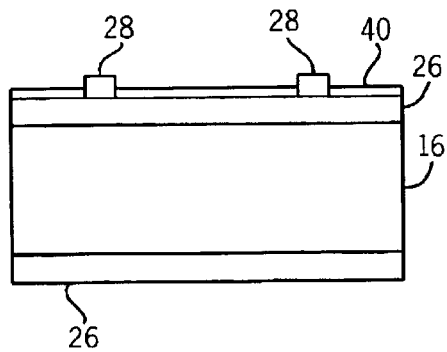

FIGS. 7A–7K illustrate, in a sequence of steps, a MEMS fabrication process for making the medicine delivery unit 14, as shown in FIGS. 1–6, in accordance with the preferred embodiment of the present invention. FIG. 7A illustrates the step of providing the substrate 16. FIG. 7B illustrates the substrate 16 having the membrane 26 applied to each opposite side of the substrate 16. In FIG. 7C, material 38 for the release element 28 is applied to the membrane 26 on one side of the substrate 16. In FIG. 7D, the material 38 for the release element 28 is selectively removed to form the release element 28. In FIG. 7E, the insulator 40 is selectively applied to the membrane 26 and the membrane material on the bottom side of the substrate 16 is selectively removed. In FIG. 7F, the medicine delivery unit 14 is turned over 180 degrees, either physically or for the sake of illustration. In FIG. 7G, the substrate 16 is etched or machined between the remaining portions of the membrane material to form the compartment 18 and the charging opening 20. In FIG. 7H, the remaining portions of the membrane material are removed. Alternatively, the remaining portions of the membrane material stay depending on the type of material. In FIG. 7I, the compartment 18 is filled with the medicine 34. In FIG. 7J, the cap 24 is disposed over the compartment 18 to seal the charging opening 20 under vacuum, according to the method described in FIG. 8. In FIG. 7K, the medicine delivery unit 14 is again turned over 180 degrees, either physically or for the sake of illustration.

Figure 8:
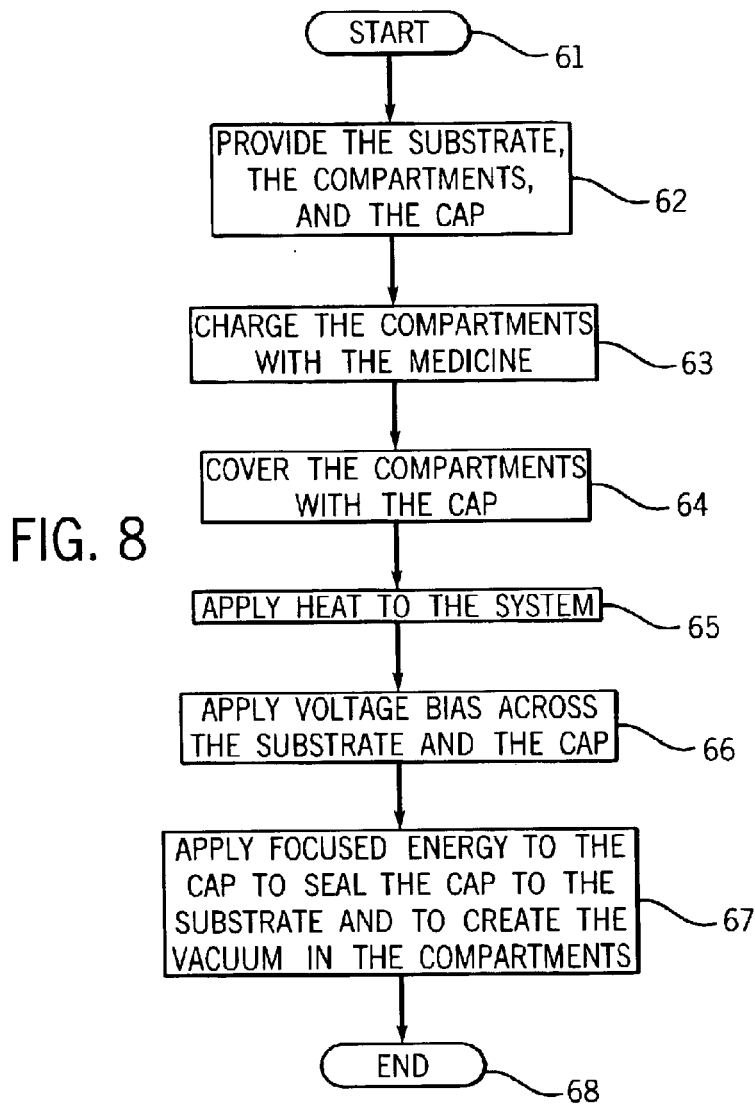
FIG. 8 illustrates a flowchart describing a method for sealing the medicine delivery unit, as shown in FIGS. 1–6, in accordance with the preferred embodiment of the present invention.

FIG. 8 illustrates a flowchart describing a method for sealing the medicine delivery unit 10, as shown in FIGS. 1–7K. The method starts at step 61. At step 62, the method provides the substrate 16, having the compartments 18, and the cap 24 in an appropriate manner for high volume manufacturing. At step 63, the method charges the compartments 18 with the medicine 34, as describe above. At step 64, the method covers the compartments 18 with the cap 24, as described above. At step 65, the method applies heat 58 to the medicine delivery system 10. In the preferred embodiment of the present invention the heat is less than 100 degrees C., which is much less than the 300–500 degrees C. temperature range used for traditional anodic bonding. At step 66, the method applies a voltage bias 56 across the substrate 16 and the cap 24. Preferably, a positive voltage is applied to the cap 24 and a negative voltage is applied to the substrate 16. Alternatively, the positive and negative voltages may be reversed, depending on the materials of the cap 24 and the substrate 16. In the preferred embodiment of the present invention, the voltage bias 56 is greater than 100 V and less than the 1 kV used for traditional anodic bonding. At step 67, the method applies focused energy 54 to the cap 24 to seal the cap 24 to the substrate 16 and to create a vacuum in the compartments 18. The focused energy 54 includes, without limitation, microwave, laser, infrared, lamps, and the like. The focused energy 54 couples into the cap 24 (e.g., at a wavelength less than 600 nm) to raise the temperature in a local area over one or more compartments 18 for the duration of an energy pulse having a microsecond to millisecond time duration. Such fast heat coupling assists in bonding the interface between the cap 24 and the substrate 16, without damaging the cap 24, the substrate 16, or the medicine 34. Silicon material conducts heat quickly and glass material and a vacuum conducts heat slowly. Therefore, when the cap 24 is made of silicon and the substrate 16 is made of glass, the focused energy 54 conducts slowly to the medicine 34. Note that the focused energy 54 does not necessarily need to be aligned with particular features of the medicine delivery system 10, depending on the size of the features, the power level and time duration of the focused energy. At step 68, the method ends. Although, the method describes a bonding process for assembly of the medicine delivery system 10, the method may be used for any kind of micromachined system or device.

The benefits of the bonding process described in the method include: a fast manufacturing throughput, uniform seals, no damage to the medicine 34, a low bonding temperature permitting more design flexibility and stable mechanical dimensions with temperature, a flat assembly process, no measurable flow of the glass material permitting sealing around previously machined grooves, cavities etc. without any loss of dimensional tolerances, parasitic capacitances are kept extremely small because the glass material is an insulator, the bonding process may be performed in vacuum permitting hermetically sealed reference cavities to be formed, transparency of the glass at optical wavelengths permits simple, but highly accurate, alignment of pre-patterned glass and silicon wafers as well as to observe the inside of micro-fluidic devices, a high yield process that is tolerant to particle contamination and wafer warp because the electrostatic field generates a high clamping force which overcomes surface irregularities, a low cost wafer scale process for first order packaging can be done at a chip level if required, multi-layer stacks permit easy routing to complex 3-D microstructures, and a high strength bond that is higher than the fracture strength of the glass material.

Figure 9:
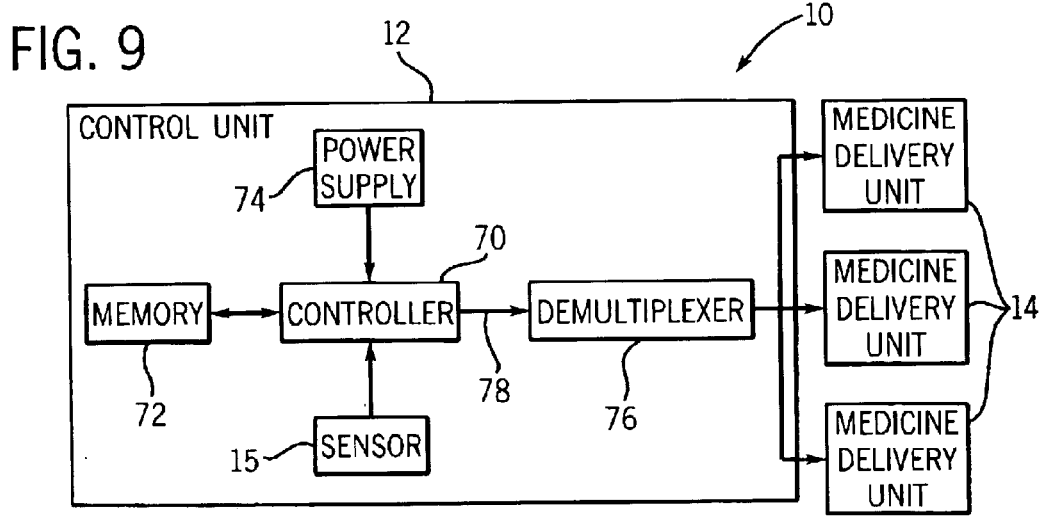
FIG. 9 illustrates a block diagram of the control unit and the medicine delivery units, as shown in FIGS. 1 and 2, in accordance with the preferred embodiment of the present invention.

FIG. 9 illustrates a block diagram of the control unit 12 and the medicine delivery units 14, as shown in FIGS. 1 and 2, in accordance with the preferred embodiment of the present invention. The medicine delivery system 10 accurately delivers medicine 34 at defined rates and times according to the needs of a human or animal patient or other experimental system. The control unit 12 includes a controller 70, a memory 72, a sensor 15, a power supply 74, and a demultiplexer 76. Preferably, the control unit 12 is constructed as an integrated circuit, but may be constructed as discrete circuits. The control unit 12 may have internal or external memory, such as RAM and/or ROM.

The power supply 74 provides power to the appropriate functions in the control unit 12, such as the controller 70. Preferably, the power supply 74 is a battery to permit portable or in body applications, and is preferably a thin film electrochemical cell deposited on the substrate 16. The criteria for selection of the power supply are small size, sufficient power capacity, ability to be integrated into the control unit 12, and, in some applications, the ability to be recharged and the length of time before recharging is necessary. Alternative batteries of this type include lithium-based, rechargeable micro-batteries that are typically only ten microns thick and occupy 1 $cm^2$ of area. One or more of these batteries can be incorporated directly into the control unit 12.

The controller 70 generates the control signal 78 to control the medicine delivery units 14. The control signal 78 may be carried on a single line carrying multiple signals, wherein each of the multiple signals is associated with a corresponding medicine delivery unit 14. Alternatively, the control signal may be carried on a plurality of lines, wherein each of the plurality of lines is associated with each medicine delivery unit 14. Hence, the controller 70 in combination with the control signal 78 actively controls the rupturing of the membrane 26 for each medicine delivery unit 14.

The control unit 12 is designed based on the period over which the medicine delivery is desired, generally in the range of at least three to twelve months for in body applications. In contrast, release times as short as a few seconds may be desirable for some applications. In some cases, continuous (constant) release from the compartment 18 may be most useful. In other cases, a pulse (bulk) release from the compartment 18 may provide more effective results. Note that a single pulse medicine delivery from one compartment 18 can be transformed into a multiple pulse medicine delivery by using multiple compartments 18. In addition, delivering several pulses of medicines in quick succession can simulate continuous medicine delivery.

The controller 70 controls the time and rate of delivery of the medicine 34 from each compartment 18 responsive to a software program or circuit, remote control, a signal from a sensor, or by any combination of these methods. Preferably, the controller 70 is used in conjunction with the sensor 15, the memory 72, the power supply 74, and the demultiplexer 76. The software program stored in the memory 72 determines the time and rate of medicine delivery. The memory 72 sends instructions to the controller 70. When the time for release has been reached as indicated by the software program, the controller 70 sends the control signal 78 corresponding to the address (location) of a particular compartment 18 to the demultiplexer 76. The demultiplexer 76 generates an electrical signal to the particular compartment 18 addressed by the controller 70.

The sensor 15 advantageously provides a closed loop feedback system to permit the medicine delivery system 10 to vary the time, rate and/or dosages of the medicine responsive to monitored conditions in the environment, such as the human or animal body.

The medicine delivery system 10 has numerous applications. The medicine delivery system 10 can be used to deliver small, controlled amounts of chemical reagents or other molecules to solutions or reaction mixtures at precisely controlled times and rates. Analytical chemistry and medical diagnostics are examples of fields where the medicine delivery system 10 can be used. The medicine delivery systems 10 can be implanted into a patient, either by surgical techniques or by injection, or can be swallowed. The medicine delivery systems 10 provide delivery of medicines to animals or persons who are unable to remember or be ambulatory enough to take medication. The medicine delivery systems 10 further provide delivery of many different medicines at varying rates and at varying times of delivery.

Hence, while the present invention has been described with reference to various illustrative embodiments thereof, the present invention is not intended that the invention be limited to these specific embodiments. Those skilled in the art will recognize that variations, modifications and combinations of the disclosed subject matter can be made without departing from the spirit and scope of the invention as set forth in the appended claims.

What is claimed is:

1. A medicine delivery system, adapted to be implanted into a human or animal body, comprising:
    a control unit adapted to generate a control signal; and
    a medicine delivery unit including:
        a plurality of compartments, each compartment adapted to contain a predetermined amount of a medicine and having a delivery opening permitting delivery of the medicine;
        a membrane adapted to seal the delivery opening of each compartment; and
        a plurality of release elements, each release element being associated respectively with the delivery opening of one of the compartments and adapted to rupture the membrane along a predetermined generally U-shaped rupture pattern responsive to the control signal to permit a first membrane portion located inside the predetermined generally U-shaped rupture pattern to separate from a second membrane portion along the predetermined generally U-shaped rupture pattern while remaining pivotally attached to the second membrane portion at a connection area, whereby the rupture of the membrane permits body fluid of the human or animal to mix with the medicine so that the medicine is released in admixture with the body fluids through the delivery opening into the human or animal body.

2. The medicine delivery system according to claim 1, wherein upon rupture of the membrane responsive to the control signal the first membrane portion form a rectangular-shaped lid and the connection area forms a hinge that extends along an attached side edge of the lid and across an open end of the generally U-shaped rupture pattern.

3. The medicine delivery system according to claim 1 further comprising:
    a substrate forming a wafer body with a plurality of spaced-apart cavities formed therein, each cavity defining a respective one of the compartments.

4. The medicine delivery system according to claim 3, wherein the membrane is integrally formed with the substrate.

5. The medicine delivery system according to claim 3, wherein the cavities each extend through the substrate to define a charging opening opposite the delivery opening for filling each compartment with the medicine, and wherein a cap is bonded to the substrate for sealing the charging openings.

6. The medicine delivery system according to claim 1, wherein the membrane has a line of weakness formed therein along the predetermined pattern to assist with rupturing the membrane and the release element is adapted to apply thermal shock to rupture the membrane in response to the control signal.

7. The medicine delivery system according to claim 1, wherein the membrane is composed of silicon.

8. The medicine delivery system according to claim 1 wherein the membrane has a predetermined elastic deformation limit and a predetermined rupture point, wherein the membrane is pre-stressed by an amount less than the predetermined elastic deformation limit and the predetermined rupture point, and wherein the release element causes the membrane to be stressed beyond the predetermined elastic deformation limit and the predetermined rupture point to rupture the membrane.

9. A medicine delivery system, adapted to be implanted into a human or animal body, comprising:
   a control unit adapted to generate a control signal; and
   a medicine delivery unit including:
     a substrate having a wafer-shape body;
     a compartment formed in the substrate for containing a predetermined amount of a medicine, the compartment having a charging opening permitting the filling of the compartment with medicine and a delivery opening permitting delivery of the medicine from the compartment;
     a cap adapted to seal the charging opening of the compartment;
     a membrane adapted to seal the delivery opening of the compartment, the membrane having a predetermined elastic deformation limit and a predetermined rupture point, and the membrane being pre-stressed by an amount less than the predetermined elastic deformation limit and the predetermined rupture point; and
     a release element associated with the compartment, the release element being adapted to cause the membrane to be stressed beyond the predetermined elastic deformation limit and the predetermined rupture point to rupture the membrane along a predetermined generally U-shaped rupture pattern responsive to the control signal to permit a first membrane portion inside the looping rupture pattern, forming a lid, to separate from a second membrane portion along the predetermined generally U-shaped rupture pattern while remaining pivotally attached to the second membrane portion at a connection area, forming a hinge, whereby the rupture of the membrane permits body fluids of the human or animal to mix with the medicine so that the medicine is released in admixture with the body fluids through the delivery opening into the human or animal body.

10. The medicine delivery system according to claim 9, wherein the membrane is integrally formed with the substrate.

11. The medicine delivery system according to claim 9, wherein the membrane has a line of weakness formed therein along the predetermined rupture pattern to assist with rupturing the membrane.

12. The medicine delivery system according to claim 9, wherein the membrane is composed of silicon.

13. The medicine delivery system according to claim 9, wherein the membrane is pre-stressed under a vacuum pressure.

14. The medicine delivery system according to claim 9, wherein the medicine is a solid.

15. The medicine delivery system according to claim 9, wherein the release element is deposited directly on the membrane and is arranged thereon in generally U-shaped pattern, the hinge extending along an attached side edge of the lid and across an open end of the generally U-shaped pattern.

16. The medicine delivery system according to claim 2, wherein the release element is deposited directly on the membrane.

* * * * *

UNITED STATES PATENT AND TRADEMARK OFFICE
CERTIFICATE OF CORRECTION

PATENT NO. : 6,953,455 B2 Page 1 of 1
DATED : October 11, 2005
INVENTOR(S) : Steven T. Cho et al.

It is certified that error appears in the above-identified patent and that said Letters Patent is hereby corrected as shown below:

Column 14,
Line 31, after "in" insert -- a --.

Signed and Sealed this

Twenty-seventh Day of December, 2005

JON W. DUDAS
*Director of the United States Patent and Trademark Office*